(12) United States Patent
Venstrom

(10) Patent No.: US 10,617,757 B2
(45) Date of Patent: Apr. 14, 2020

(54) METHODS FOR TREATING MULTIPLE MYELOMA

(71) Applicant: The Regents of the University of California, Oakland, CA (US)

(72) Inventor: Jeffrey M. Venstrom, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 15/502,182

(22) PCT Filed: Aug. 4, 2015

(86) PCT No.: PCT/US2015/043656
§ 371 (c)(1),
(2) Date: Feb. 6, 2017

(87) PCT Pub. No.: WO2016/022589
PCT Pub. Date: Feb. 11, 2016

(65) Prior Publication Data
US 2017/0224817 A1 Aug. 10, 2017

Related U.S. Application Data

(60) Provisional application No. 62/035,304, filed on Aug. 8, 2014.

(51) Int. Cl.
| | | |
|---|---|---|
| A61K 39/395 | (2006.01) | |
| C07K 16/28 | (2006.01) | |
| C12Q 1/6881 | (2018.01) | |
| A61K 31/454 | (2006.01) | |
| A61K 31/573 | (2006.01) | |
| C07K 16/30 | (2006.01) | |
| C12Q 1/6886 | (2018.01) | |

(52) U.S. Cl.
CPC ...... *A61K 39/39558* (2013.01); *A61K 31/454* (2013.01); *A61K 31/573* (2013.01); *C07K 16/2896* (2013.01); *C07K 16/3061* (2013.01); *C12Q 1/6881* (2013.01); *C12Q 1/6886* (2013.01); *C07K 2317/24* (2013.01); *C07K 2317/51* (2013.01); *C07K 2317/56* (2013.01); *C07K 2317/565* (2013.01); *C07K 2317/567* (2013.01); *C07K 2317/732* (2013.01); *C07K 2317/92* (2013.01); *C12Q 2600/106* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

2010/0092489 A1* 4/2010 Van De Winkel .......................... A61K 39/39558
424/172.1
2011/0262454 A1* 10/2011 Park .................. A61K 47/6867
424/158.1

FOREIGN PATENT DOCUMENTS

| WO | WO 2005/009466 | 2/2005 |
| WO | WO 2008/047242 | 4/2008 |
| WO | WO 2010/061357 | 6/2010 |
| WO | WO 2010/061358 | 6/2010 |
| WO | WO 2010/061360 | 6/2010 |
| WO | WO 2012/071411 | 5/2012 |
| WO | WO 2012/076663 | 6/2012 |
| WO | WO 2013/155346 | 10/2013 |
| WO | WO 2014/089416 | 6/2014 |
| WO | WO 2014/159911 | 10/2014 |

OTHER PUBLICATIONS

Gabriel et al. (Blood, Sep. 23, 2010, vol. 116, No. 12, pp. 2033-2039) (Year: 2010).*
Giglio et al. (54th ASH Annual Meeting Exposition, Abstract 349, Dec. 10, 2012) (Year: 2012).*
De Weers, et al.; "Daratumumab, a Novel Therapeutic Human CD38 Monoclonal Antibody, Induces Killing of Multiple Myeloma and Other Hematological Tumors"; The Journal of Immunology; vol. 186, pp. 1840-1848 (Dec. 2010).
Gabriel, et al.; "Interaction between KIR3DS1 and HLA-Bw4 predicts for progression-free survival after autologous stem cell transplantation in patients with multiple myeloma"; Blood; vol. 116, No. 12, pp. 2033-2039 (Sep. 2010).
Giglio, et al.; "Donor KIR3DL1 and HLA-B Allotypes Control Leukemia Relapse After Allogeneic Hematopoietic Stem Cell Transplantation"; Abstract 349, 54th ASH Annual Meeting and Exposition, Atlanta, GA. Session: 723. Clinical Allogeneic and Autologous Transplantation: Late Complications and Approaches to Disease Recurrence: Improving Transplant Outcomes Through Immunomodulation. Monday, Dec. 10, 2012; 7:00 AM (3 pages).
Kim, et al.; "HLA alleles determine differences in human natural killer cell responsiveness and potency"; PNAS; vol. 105, No. 8, pp. 3053-3058 (Feb. 26, 2008).

(Continued)

*Primary Examiner* — Meera Natarajan
(74) *Attorney, Agent, or Firm* — Bozicevic Field & Francis, LLP; Paula A. Borden

(57) ABSTRACT

The present disclosure provides methods of treating multiple myeloma in an individual, the methods comprising genotyping an HLA allele and a KIR allele in the individual; and, depending on the outcome of the genotyping, administering a multiple myeloma therapy to the individual. In some embodiments, the multiple myeloma therapy comprises an anti-CD38 antibody, lenalidomide, and dexamethasone. The present disclosure provides methods for selecting a multiple myeloma patient for a multiple myeloma therapy. The present disclosure provides methods for identifying a multiple myeloma patient as likely to experience a beneficial clinical outcome from a multiple myeloma therapy.

9 Claims, 8 Drawing Sheets
Specification includes a Sequence Listing.

(56) References Cited

OTHER PUBLICATIONS

Venstrom, et al.; "KIR and HLA Genotypes Are Associated with Disease Progression. and Survival following Autologous Hematopoietic Stem Cell Transplantation for High-Risk Neuroblastoma"; Clin. Cancer Res.; vol. 15, pp. 7330-7334 (Nov. 24, 2009).

* cited by examiner

METHODS FOR TREATING MULTIPLE MYELOMA

CROSS-REFERENCE

This application is a national phase application under 35 U.S.C. § 371 of PCT/US2015/043,656, filed Aug. 4, 2015, which claims the benefit of U.S. Provisional Patent Application No. 62/035,304, filed Aug. 8, 2014, which applications are incorporated herein by reference in their entirety.

INCORPORATION BY REFERENCE OF SEQUENCE LISTING PROVIDED AS A TEXT FILE

A Sequence Listing is provided herewith as a text file, "UCSF-501WO SeqList_ST25.txt" created on Aug. 3, 2015 and having a size of 12 KB. The contents of the text file are incorporated by reference herein in their entirety.

INTRODUCTION

CD38 is a 45 kD type II transmembrane glycoprotein that is upregulated in many hematopoietic malignancies and in cell lines derived from various hematopoietic malignancies.

Multiple myeloma (MM) is a B cell malignancy. In MM, abnormal plasma cells accumulate in the bone marrow where they interfere with the production of normal cells. Current therapy of MM includes administration of proteasome inhibitors such as bortezomib, immunomodulatory drugs such as lenalidomide and thalidomide, and chemotherapy such as melphalan and prednisone. While these agents have improved survival in multiple myeloma, resistance can occur and patients can succumb from their illness. Multiple myeloma is thus frequently fatal, with a median survival of approximately 3 to 5 years.

SUMMARY

The present disclosure provides methods of treating multiple myeloma in an individual, the methods comprising genotyping an HLA allele and a KIR allele in the individual; and, depending on the outcome of the genotyping, administering an anti-CD38 antibody to the individual. The present disclosure provides methods for selecting a multiple myeloma patient for anti-CD38 antibody therapy. The present disclosure provides methods for identifying a multiple myeloma patient as likely to experience a beneficial clinical outcome from an anti-CD38 therapy.

The present disclosure provides a method of treating an individual having multiple myeloma, the method comprising: a) determining a genotype of a KIR allele of the individual; b) determining a genotype of an HLA allele of the individual, and c) when said determining of steps (a) and (b) indicates that the individual has a 3DL1 KIR allele and an HLA-B Bw4-I80 allele, administering a treatment to the individual, wherein the treatment comprises an anti-CD38 antibody, lenalidomide, and dexamethasone. In some cases, the anti-CD38 antibody competes for binding to an epitope in CD38 with an antibody that comprises VH complementarity determining regions (CDRs) present in SEQ ID NO:7 and VL CDRs present in SEQ ID NO:8. In some cases, the anti-CD38 antibody competes for binding to an epitope in CD38 with an antibody that comprises VH CDR1 of SEQ ID NO:1 (DYWMQ), VH CDR2 of SEQ ID NO:2 (TI-YPGDGDTGYAQKFQG), VH CDR3 of SEQ ID NO:3 (GDYYGSNSLDY), VL CDR1 of SEQ ID NO:4 (KASQD-VSTVVA), VL CDR2 of SEQ ID NO:5 (SASYRYI), and VL CDR3 of SEQ ID NO:6 (QQHYSPPYT). In some cases, the anti-CD38 antibody comprises VH CDR1 of SEQ ID NO:1 (DYWMQ), VH CDR2 of SEQ ID NO:2 (TI-YPGDGDTGYAQKFQG), VH CDR3 of SEQ ID NO:3 (GDYYGSNSLDY), VL CDR1 of SEQ ID NO:4 (KASQD-VSTVVA), VL CDR2 of SEQ ID NO:5 (SASYRYI), and VL CDR3 of SEQ ID NO:6 (QQHYSPPYT). In some cases, the anti-CD38 antibody comprises VH CDRs present in SEQ ID NO:7 and VL CDRs present in SEQ ID NO:8. In some cases, the anti-CD38 antibody kills a CD38+ cell by apoptosis, by antibody-dependent cell-mediated cytotoxicity (ADCC), or by complement-dependent cytotoxicity (CDC). In some cases, the anti-CD38 antibody binds CD38 with a kD of $3 \times 10^{-9}$ or greater. In some cases, the anti-CD38 antibody comprises a humanized heavy chain framework region and/or a humanized light chain framework region. In some cases, the anti-CD38 antibody comprises a VH region comprising the amino acid sequence set forth in SEQ ID NO:7, and comprises a VL region comprising the amino acid sequence set forth in SEQ ID NO:8. In some cases, the anti-CD38 antibody comprises a heavy chain region of the isotype IgG1, IgG2, IgG3, or IgG4. In some cases, the method further comprises determining the copy number of the HLA-B Bw4-I80 allele. In some cases, said administering increases progression-free survival (PFS). In some cases, said administering increases time to progression (TTP). In some cases, the multiple myeloma is relapsed refractory multiple myeloma.

The present disclosure provides a method of selecting an individual for a therapy comprising administering an anti-CD38 antibody, lenalidomide, and dexamethasone, wherein the individual has multiple myeloma, the method comprising: a) determining a genotype of a KIR allele in a biological sample obtained from the individual; b) determining a genotype of an HLA allele in a biological sample obtained from the individual; and c) selecting the individual for the therapy if determining of steps (a) and (b) indicates that the individual has a 3DL1 KIR allele and an HLA-B Bw4-I80 allele. In some cases, the multiple myeloma is relapsed refractory multiple myeloma. In some cases, the biological sample a nucleated blood cell or a peripheral blood lymphocyte.

The present disclosure provides a method of determining the likelihood that an individual having multiple myeloma will exhibit a beneficial clinical response to a treatment wherein the treatment comprises an anti-CD38 antibody, lenalidomide, and dexamethasone, the method comprising: a) determining a genotype of a killer Ig-like receptor (KIR) allele of the individual; b) determining a genotype of a human leukocyte antigen (HLA) allele of the individual, wherein the presence of a 3DL1 KIR allele, and the presence of an HLA Bw4-I80 allele, indicate that the individual has a greater likelihood of exhibiting a beneficial clinical response to the treatment, compared to an individual who does not have a KIR3DL1 allele and an HLA-B Bw4-I80 allele. In some cases, the multiple myeloma is relapsed refractory multiple myeloma. In some cases, the method comprises recommending a treatment regimen based on the determined likelihood.

The present disclosure provides an active agent comprising anti-CD38 antibody, lenalidomide, and dexamethasone for use in method of treatment of an individual having multiple myeloma, the method comprising: a) determining a genotype of a KIR allele of the individual; b) determining a genotype of an HLA allele of the individual, and c) when said determining of steps (a) and (b) indicates that the individual has a 3DL1 KIR allele and an HLA-B Bw4-I80 allele, administering said anti-CD38 antibody, lenalidomide, and dexamethasone to the individual. In some cases, the anti-CD38 antibody, lenalidomide, and dexamethasone are administered by different routes of administration. In some cases, the anti-CD38 antibody competes for binding to an epitope in CD38 with an antibody that comprises VH complementarity determining regions (CDRs) present in SEQ ID NO:7 and VL CDRs present in SEQ ID NO:8. In some cases, the anti-CD38 antibody (i) competes for binding to an epitope in CD38 with an antibody that comprises VH CDR1 of SEQ ID NO:1 (DYWMQ), VH CDR2 of SEQ ID NO:2 (TIYPGDGDTGYAQKFQG), VH CDR3 of SEQ ID NO:3 (GDYYGSNSLDY), VL CDR1 of SEQ ID NO:4 (KASQDVSTVVA), VL CDR2 of SEQ ID NO:5 (SASYRYI), and VL CDR3 of SEQ ID NO:6 (QQHYSPPYT); or (ii) comprises VH CDR1 of SEQ ID NO:1 (DYWMQ), VH CDR2 of SEQ ID NO:2 (TIYPGDGDTGYAQKFQG), VH CDR3 of SEQ ID NO:3 (GDYYGSNSLDY), VL CDR1 of SEQ ID NO:4 (KASQDVSTVVA), VL CDR2 of SEQ ID NO:5 (SASYRYI), and VL CDR3 of SEQ ID NO:6 (QQHYSPPYT). In some cases, the anti-CD38 antibody comprises VH CDRs present in SEQ ID NO:7 and VL CDRs present in SEQ ID NO:8. In some cases, the anti-CD38 antibody kills a $CD38^+$ cell by apoptosis, by ADCC, or by CDC. In some cases, the anti-CD38 antibody binds CD38 with a kD of $3 \times 10^{-9}$ or greater. In some cases, the anti-CD38 antibody comprises a humanized heavy chain framework region and/or a humanized light chain framework region. In some cases, the anti-CD38 antibody comprises a VH region comprising the amino acid sequence set forth in SEQ ID NO:7, and comprises a VL region comprising the amino acid sequence set forth in SEQ ID NO:8. In some cases, the anti-CD38 antibody comprises a heavy chain region of the isotype IgG1, IgG2, IgG3, or IgG4. In some cases, the method further comprises determining the copy number of the HLA-B Bw4-I80 allele. In some cases, said administering increases PFS. In some cases, said administering increases TTP. In some cases, the multiple myeloma is relapsed refractory multiple myeloma.

DEFINITIONS

Figure 1:
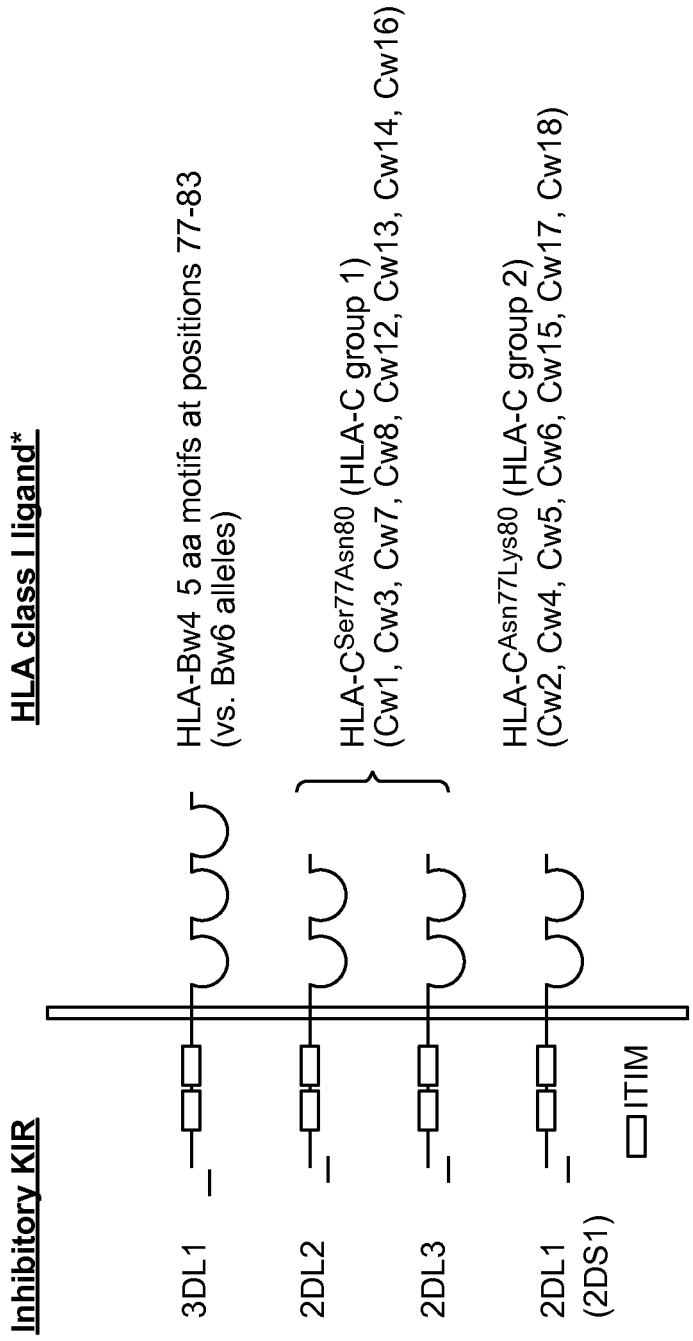
FIG. 1 shows the types of inhibitory Killer Immunoglobulin-like Receptors (KIRs) and Human Leukocyte Antigen (HLA) class I ligands that determine the variability of Natural Killer (NK) cell function.

The term "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The term "genotype" refers to the specific allelic composition of an entire cell or a certain gene and in some aspects a specific polymorphism associated with that gene, whereas the term "phenotype' refers to the detectable outward manifestations of a specific genotype.

As used herein, the term "determining the genotype of a cell or tissue sample" intends to identify the genotypes of polymorphic loci of interest in the cell or tissue sample. For example, "determining the genotype" can comprise determining an allele, e.g., a KIR allele and/or an HLA allele.

When a genetic marker or polymorphism "is used as a basis or to aid in determination of, or for selecting a patient for a treatment described herein, the genetic marker or polymorphism can be measured before and/or during treatment, and the values obtained can be used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one skilled in the art, measurement of the genetic marker or polymorphism in a clinical setting is a clear indication that this parameter can be used as a basis for initiating, continuing, adjusting and/or ceasing administration of the treatments described herein.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. In some cases, the biological sample comprises nucleated cells. A suitable biological sample can comprise peripheral blood lymphocytes. A suitable biological sample can comprise blood cells, e.g., nucleated blood cells such as lymphocytes, etc.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, can include treatment of a disease in a mammal, particularly in a human, such as: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. For example, in the case of cancer, a response to treatment can include a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs.

A "therapeutically effective amount" or "efficacious amount" refers to the amount of an agent (e.g., antibody; small molecule; etc.) that, when administered to a mammal or other subject for treating a disease, is sufficient to effect such treatment for the disease. The amount is empirically determined by the patient's clinical parameters including, but not limited to the stage of disease, age, gender, histology, and likelihood for tumor recurrence.

The term "clinical outcome", "clinical parameter", "clinical response", or "clinical endpoint" refers to any clinical observation or measurement relating to a patient's disease status over time in the absence of or in response to a therapy. Non-limiting examples of clinical outcomes include tumor response (TR), overall survival (OS), progression free survival (PFS), disease free survival (DFS), progression free survival (PFS), time to tumor recurrence (TTR), time to tumor progression (TTP), relative risk (RR), and toxicity or side effects.

As used herein in the context of patient response to a treatment (e.g., a treatment regimen that includes an anti-CD38 antibody), the terms "beneficial response," "beneficial patient response," and "clinically beneficial response," "clinical benefit," and the like, are used interchangeably and refer to favorable patient response to a treatment (e.g., a treatment regimen that includes an anti-CD38 antibody) as opposed to unfavorable responses, i.e. adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; PFS; TTP; and/or decreased mortality at a given point of time following treatment. Continued increase in tumor size and/or cancer cell number and/or tumor metastasis and/or shortened PFS and/or shortened TTP is indicative of lack of beneficial response to treatment.

The term "likely to respond" intends to mean that the patient of a genotype is relatively more likely to experience a more favorable outcome as compared to patients similarly situated without the genotype. Alternatively, the term "not likely to respond" intends to mean that the patient of a genotype is relatively less likely to experience a favorable outcome than patients similarly situated without the genotype.

The term "suitable for a therapy" or "suitably treated with a therapy" shall mean that the patient is likely to exhibit one or more desirable clinical outcome as compared to patients having the same disease and receiving the same therapy but possessing a different characteristic that is under consideration for the purpose of the comparison. In one aspect, the characteristic under consideration is an allele (e.g., a KIR3DL1 allele; an HLA-B Bw4-I80 allele). In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcome is considered simultaneously. In one such aspect, a patient possessing a characteristic, such as a genotype of a genetic polymorphism, may exhibit more than one more desirable clinical outcomes as compared to patients having the same disease and receiving the same therapy but not possessing the characteristic. As defined herein, the patient possessing the characteristic can be considered suitable for the therapy. In another such aspect, a patient possessing a characteristic may exhibit one or more desirable clinical outcome but simultaneously exhibit one or more less desirable clinical outcome. The clinical outcomes can be considered collectively, and a decision as to whether the patient is suitable for the therapy can be made accordingly, taking into account the patient's specific situation and the relevance of the clinical outcomes. In some embodiments, progression free survival or overall survival is weighted more heavily than tumor response in a collective decision making.

"Progressive disease" (PD) indicates that the tumor has grown (i.e. become larger), spread (i.e. metastasized to another tissue or organ) or the overall cancer has gotten worse following treatment. For example, tumor growth of more than 20 percent since the start of treatment typically indicates progressive disease.

"Disease free survival" (DFS) indicates the length of time after treatment of a cancer or tumor during which a patient survives with no signs of the cancer or tumor.

"Non-response" (NR) to a therapy defines patients whose tumor or evidence of disease has remained constant or has progressed.

"Overall Survival" (OS) intends a prolongation in life expectancy as compared to naïve or untreated individuals or patients.

"Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease.

"No Correlation" refers to a statistical analysis showing no relationship between the allelic variant of a polymorphic region or gene expression levels and clinical parameters.

"Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer.

"Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up.

"Relative Risk" (RR), in statistics and mathematical epidemiology, refers to the risk of an event (or of developing a disease) relative to exposure. Relative risk is a ratio of the probability of the event occurring in the exposed group versus a non-exposed group.

A "tumor" is an abnormal growth of tissue resulting from uncontrolled, progressive multiplication of cells and serving no physiological function. A "tumor" is also known as a neoplasm.

The term "hazard ratio" is a survival analysis in the effect of an explanatory variable on the hazard or risk of an event. In another aspect, "hazard ratio" is an estimate of relative risk, which is the risk of an event or development of a disease relative to treatment and in some aspects the expression levels of the gene of interest. Statistical methods for determining hazard ratio are well known in the art.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), a cytotoxic agent, and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent. In some cases, an antibody provides for an ADCC, CMC, or a direct apoptotic effect on a target cell.

The term "humanized antibody" as used herein refers to an antibody comprising portions of antibodies of different origin, wherein at least one portion comprises amino acid sequences of human origin. For example, the humanized antibody can comprise portions derived from an antibody of nonhuman origin with the requisite specificity, such as a mouse, and from antibody sequences of human origin (e.g., chimeric antibody), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized antibody is an antibody containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized antibody. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized antibodies can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$ and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

The terms "individual," "subject," "host," and "patient," used interchangeably herein, refer to a mammal, e.g., a human.

As used herein, relapsed multiple myeloma refers to clinical criteria developed by the International Myeloma Working Group (IMWG) which includes one or more of: direct indicators of increasing disease and/or end organ dysfunction (CRAB features, for progressive disease, serum M-component increases of >1 gm/dL are sufficient to define relapse if starting M-component is ≤5 g/dL), development of new soft tissue plasmacytomas or bone lesions, definite increase in the size of existing plasmacytomas or bone lesions, a definite increase is defined as a 50% (and at least 1 cm) increase as measured serially by the sum of the products of the cross-diameters of the measurable lesion, hypercalcemia (>11.5 mg/dL) [2.65 mmol/L], decrease in haemoglobin of ≤2 g/dL [1.25 mmol/L], rise in serum creatinine by 2 mg/dL or more [177 mmol/L or more].

As used herein refractory multiple myeloma refers to progressive or stable multiple myeloma while being treated with a given therapeutic treatment for the disease.

As used herein, "lenalidomide," or a "lenalidomide compound" refers to lenalidomide ((RS)-3-(4-amino-1-oxo-3H-isoindol-2-yl)piperidine-2,6-dione), as shown below:

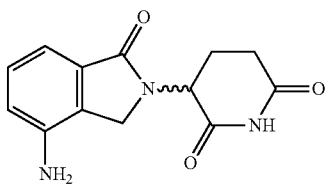 [SMILES: Nc1cccc2c1CN(C1CCC(=O)NC1=O)C2=O]

As used herein, "dexamethasone" refers to a compound of the structure:

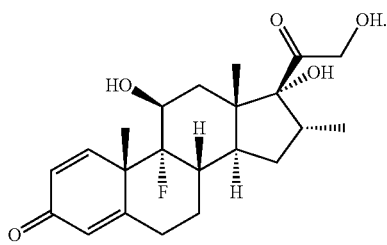

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a KIR genotype" includes a plurality of such genotypes and reference to "the anti-CD38 antibody" includes reference to one or more anti-CD38 antibodies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

It has been found that KIR3DL1, HLA-B Bw4-80Ile genotype predictive of high-affinity NK cell receptor-ligand interactions and potent NK cell licensing correlate with increased objective overall response rate (ORR) and progression free survival (PFS) among patients treated with a combination of SAR650984 (a humanized anti-CD38 antibody), lenalidomide, and dexamethasone.

The present disclosure provides methods of treating multiple myeloma (MM) in an individual, the methods comprising genotyping an HLA allele and a KIR allele in the individual; and, depending on the outcome of the genotyping, administering a multiple myeloma therapy to the individual. The present disclosure provides methods for selecting a multiple myeloma patient for a multiple myeloma therapy. The present disclosure provides methods for identifying a multiple myeloma patient as likely to experience a beneficial clinical outcome from multiple myeloma therapy. A multiple myeloma therapy can include, e.g., monotherapy with an anti-CD38 antibody; combination therapy with an anti-CD38 antibody (e.g., SAR650984), lenalidomide, and dexamethasone; and the like.

Treatment Methods

The present disclosure provides methods of treating multiple myeloma in an individual, the methods comprising genotyping an HLA allele and a KIR allele in the individual; and, depending on the outcome of the genotyping, administering a multiple myeloma therapy to the individual. For example, the present disclosure provides a method of treating multiple myeloma in an individual, the method comprising: a) determining a genotype of a KIR allele of the individual; b) determining a genotype of an HLA allele of the individual, and c) when said determining of steps (a) and (b) indicates that the individual has a 3DL1 KIR allele and an HLA-B Bw4-I80 allele, administering an effective amount of a multiple myeloma therapy to the individual.

The present disclosure provides methods of treating multiple myeloma in an individual, the methods comprising genotyping an HLA allele and a KIR allele in the individual; and, depending on the outcome of the genotyping, administering an anti-CD38 antibody to the individual. For example, the present disclosure provides a method of treating multiple myeloma in an individual, the method comprising: a) determining a genotype of a KIR allele of the individual; b) determining a genotype of an HLA allele of the individual, and c) when said determining of steps (a) and (b) indicates that the individual has a 3DL1 KIR allele and an HLA-B Bw4-I80 allele, administering an effective amount of an anti-CD38 antibody to the individual.

The present disclosure provides a method of treating an individual having multiple myeloma, the method comprising: a) determining a genotype of a KIR allele of the individual; b) determining a genotype of an HLA allele of the individual, and c) when said determining of steps (a) and (b) indicates that the individual has a 3DL1 KIR allele and an HLA-B Bw4-I80 allele, administering a treatment to the individual, wherein the treatment comprises administering, in combination therapy, combined effective amounts of an anti-CD38 antibody, lenalidomide, and a corticosteroid such as dexamethasone.

In some cases, the method involves determining the copy number of the HLA-B Bw4-I80 allele. A single copy of the HLA-B Bw4-I80 allele is correlated with a beneficial clinical outcome; the presence of two copies of the HLA-B Bw4-I80 allele is correlated with a greater likelihood of beneficial clinical outcome.

Beneficial clinical outcomes include increased progression-free survival (PFS); increased time to progression (TTP), and the like.

In some cases, the multiple myeloma is relapsed refractory multiple myeloma.

An anti-CD38 antibody, lenalidomide, and dexamethasone are referred to individually and collectively as an "active agent." An active agent is administered in a composition, e.g., a pharmaceutical composition. In some instances, a composition comprising an active agent can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

An active agent can be administered to an individual using any available conventional methods and routes suitable for delivery of conventional drugs, including systemic or localized routes. In general, suitable routes of administration include, but are not necessarily limited to, enteral, parenteral, or inhalational routes. Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the active agent. Where systemic delivery is desired, administration typically involves invasive or systemically absorbed topical or mucosal administration of pharmaceutical preparations.

An active agent can also be delivered to an individual by enteral administration. Enteral routes of administration include, but are not necessarily limited to, oral and rectal (e.g., using a suppository) delivery.

An active agent can be administered locally to the area in need of treatment; this may be achieved by, for example, and not by way of limitation, local infusion, e.g., by injection or by means of a catheter.

Where two or more active agents are administered, the two or more active agents can be administered by the same or different routes of administration.

An active agent such as an anti-CD38 antibody can be provided to a patient as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject® NovoPen®, B-D®Pen, AutoPen®, and Opti-Pen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

The daily dosage of an active agent will vary with the agent employed, the mode of administration, the treatment desired and the disease indicated, as well as other factors such as a subject's age, body weight, general health, condition, prior medical history and sex, and like factors known in the medical arts. For example, in some cases, an active agent is administered at a daily dosage in the range from about 0.5 mg/kg body weight to about 15 mg/kg body weight, e.g. in the range from about 1 mg/kg body weight to about 10 mg/kg body weight. As another example, in some cases, an active agent is administered at a daily dosage from about 0.001 g to about 1.5 g, e.g., not exceeding about 1 gram, e.g. from about 0.1 g to about 0.5 g for a 70 kg human, given up to 4 times daily.

An active agent is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

In some cases, multiple doses of an active agent are administered. For example, an active agent is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). In some cases, an active agent is administered substantially continuously, or continuously, over a period of time ranging from about one day to about one week, from about two weeks to about four weeks, from about one month to about two months, from about two months to about four months, from about four months to about six months, or more.

Anti-CD38 Antibodies

In addition to SAR650984, suitable anti-CD38 antibodies include antibodies that specifically bind an epitope in a CD38 polypeptide. Suitable anti-CD38 antibodies include anti-CD38 antibodies known in the art and described in, e.g., WO 2008/047242; WO 2011/154453; U.S. Pat. No. 8,153,765; WO 2007/042309, and WO 2006/099875. For example, in some embodiments, a suitable anti-CD38 antibody can be daratumumab (see, e.g., deWeers et al. (2010) J. Immunol. 186:1840). In some embodiments, suitable anti-CD38 antibody can be MOR202.

In some cases, a suitable anti-CD38 antibody competes for binding to an epitope in CD38 with an antibody that comprises VH complementarity determining regions (CDRs) present in SEQ ID NO:7 and VL CDRs present in SEQ ID NO:8.

SEQ ID NO: 7:

(SEQ ID NO: 7)
QVQLVQSGAEVAKPGTSVKLSCKASGYTFTDYWMQWVKQRPGQGLEWIGT

IYPGDGDTGYAQKFQGKATLTADKSSKTVYMHLSSLASEDSAVYYCARGD

YYGSNSLDYWGQGTSVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

K.

SEQ ID NO: 8:

(SEQ ID NO: 8)
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some cases, a suitable anti-CD38 antibody competes for binding to an epitope in CD38 with an antibody that comprises VH CDR1 of SEQ ID NO:1 (DYWMQ), VH CDR2 of SEQ ID NO:2 (TIYPGDGDTGYAQKFQG), VH CDR3 of SEQ ID NO:3 (GDYYGSNSLDY), VL CDR1 of SEQ ID NO:4 (KASQDVSTVVA), VL CDR2 of SEQ ID NO:5 (SASYRYI), and VL CDR3 of SEQ ID NO:6 (QQHYSPPYT).

In some cases, a suitable anti-CD38 antibody comprises VH CDR1 of SEQ ID NO:1 (DYWMQ), VH CDR2 of SEQ ID NO:2 (TIYPGDGDTGYAQKFQG), VH CDR3 of SEQ ID NO:3 (GDYYGSNSLDY), VL CDR1 of SEQ ID NO:4 (KASQDVSTVVA), VL CDR2 of SEQ ID NO:5 (SASYRYI), and VL CDR3 of SEQ ID NO:6 (QQHYSPPYT). SAR650984 comprises VH and VL CDR sequences set forth in SEQ ID NOs:1-6.

In some cases, a suitable anti-CD38 antibody comprises VH CDRs present in SEQ ID NO:7 and VL CDRs present in SEQ ID NO:8.

In some cases, a suitable anti-CD38 antibody comprises a VH region comprising the amino acid sequence set forth in SEQ ID NO:7, and comprises a VL region comprising the amino acid sequence set forth in SEQ ID NO:8.

In some cases, a suitable anti-CD38 antibody competes for binding to an epitope in CD38 with an antibody that comprises VH CDR1 of SEQ ID NO:9 (SFAMS), VH CDR2 of SEQ ID NO:10 (AISGSGGGTYYADSVK), VH CDR3 of SEQ ID NO:11 (DKILWFGEPVFDY), VL CDR1 of SEQ ID NO:12 (RASQSVSSYLA), VL CDR2 of SEQ ID NO:13 (DASNRAT), and VL CDR3 of SEQ ID NO:14 (QQRSNWPPTF).

In some cases, a suitable anti-CD38 antibody comprises VH CDR1 of SEQ ID NO:9 (SFAMS), VH CDR2 of SEQ ID NO:10 (AISGSGGGTYYADSVK), VH CDR3 of SEQ ID NO:11 (DKILWFGEPVFDY), VL CDR1 of SEQ ID NO:12 (RASQSVSSYLA), VL CDR2 of SEQ ID NO:13 (DASNRAT), and VL CDR3 of SEQ ID NO:14 (QQRSNWPPTF).

In some embodiments, a suitable anti-CD38 antibody kills a CD38$^+$ cell by apoptosis, by antibody-dependent cell-mediated cytotoxicity (ADCC), or by complement-dependent cytotoxicity (CDC). In some embodiments, a suitable anti-CD38 antibody kills a CD38$^+$ cell by apoptosis, ADCC, and CDC.

A suitable anti-CD38 antibody binds CD38 with a kD of from about $10^{-8}$ M to about $5\times10^{-8}$ M, from about $5\times10^{-8}$ M to about $10^{-9}$ M, from about $10^{-9}$ M to about $5\times10^{-9}$ M, from about $5\times10^{-9}$ M to about $10^{-10}$ M, from about $10^{-10}$ M to about $5\times10^{-10}$ M, from about $5\times10^{-10}$ M to about $10^{-11}$ M, or greater.

A suitable anti-CD38 antibody can include a humanized heavy chain framework region. A suitable anti-CD38 antibody can include a humanized light chain framework region. A suitable anti-CD38 antibody can include both a humanized heavy chain framework region and humanized light chain framework region. In some cases, a suitable anti-CD38 antibody does not substantially induce an immune response in a human to the anti-CD38 antibody.

In some cases, a suitable anti-CD38 antibody comprises a heavy chain region of the isotype IgG1, IgG2, IgG3, or IgG4. In some cases, a suitable anti-CD38 antibody comprises an IgG1 heavy chain isotype. In some cases, a suitable anti-CD38 antibody comprises a human IgG1 heavy chain isotype.

Genotyping Methods

Determination of genotype of a KIR allele or an HLA allele in a biological sample obtained from an individual can be carried out using any convenient method, a number of which are well known in the art. Determination of the genotype of a KIR allele or an HLA allele can be carried out using genomic DNA. Determination of the genotype of a KIR allele or an HLA allele can be carried out using mRNA, or a cDNA copy of mRNA.

KIR3DL1 polypeptides, and nucleotide sequences encoding same, are known in the art. See, e.g., Yindom et al. (2014) Tissue Antigens 83:124; Sun et al. (2008) Tissue Antigens 72:578; Gardiner et al. (2001) J. Immunol. 166: 2992; and Hou et al. (2012) Methods Mol. Biol. 882:431. The available information can be used to determine the genotype of a KIR allele, e.g., a KIR3DL1 allele.

HLA polypeptides, and nucleotide sequences encoding same, are known in the art. For example, HLA Bw4 polypeptides, and nucleotide sequences encoding same, are known in the art. The available information can be used to determine the genotype of an HLA allele, e.g., to determine an HLA-Bw4-I80 allele. See, e.g., GenBank Accession No. Q95365; Adams et al. (1995) Tissue Antigens 45:18; Cox et al. (2003) Tissue Antigens 61:20; Steiner et al. (1997) Hum. Immunol. 56:84; Balas et al. (1999) Tissue Antigens 53:374; Steiner et al. (2001) Tissue Antigens 57:373; Garcia-Sanchez et al. (2002) Tissue Antigens 59:47; and Muller et al. (1989) Immunogenetics 30:200. See, e.g., SEQ ID NO:15, where I80 is amino acid 104, given that the mature protein begins with amino acid 25.

Detection of point mutations or additional base pair repeats can be accomplished by molecular cloning of the specified allele and subsequent sequencing of that allele using techniques known in the art, in some aspects, after isolation of a suitable nucleic acid sample using methods known in the art. Alternatively, the gene sequences can be amplified directly from a genomic DNA preparation from the tumor tissue using polymerase chain reaction (PCR), and the sequence composition is determined from the amplified product. As described more fully below, numerous methods are available for isolating and analyzing a subject's DNA for mutations at a given genetic locus such as the gene of interest (KIR allele; HLA allele).

A suitable detection method is allele specific hybridization using probes overlapping the polymorphic site and having about 5, or alternatively 10, or alternatively 20, or alternatively 25, or alternatively 30 nucleotides around the polymorphic region. In another embodiment of the disclosure, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (1997) Proc. Natl. Acad. Sci, USA 74:560) or Sanger et al. (1977) Proc. Nat. Acad. Sci, 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO 94/16101, entitled DNA Sequencing by Mass Spectrometry by Koster; U.S. Pat. No. 5,547,835 and international patent application Publication Number WO 94/21822 entitled "DNA Sequencing by Mass Spectrometry Via Exonuclease Degradation" by Koster; U.S. Pat. No. 5,605,798 and International Patent Application No. PCT/US96/03651 entitled DNA Diagnostics Based on Mass Spectrometry by Koster; Cohen et al. (1996) Adv. Chromat. 36:127-162; and Griffin et al. (1993) Appl. Biochem. Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In other embodiments, alteration in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc. Natl. Acad. Sci USA 86:2766; Cotton (1993) Mutat. Res. 285:125-144 and Hayashi (1992) Genet Anal Tech. Appl. 9:73-79). Single-stranded DNA fragments of sample and control nucleic acids are denatured and allowed to renature. The secondary structure of single-stranded nucleic acids varies according to sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR.

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant disclosure. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell Probes 6:1).

In another embodiment, identification of the allelic variant is carried out using an oligonucleotide ligation assay (OLA), as described, e.g., in U.S. Pat. No. 4,998,617 and in Landegren et al. (1988) Science 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al. have described a nucleic acid detection assay that combines attributes of PCR and OLA (Nickerson et al. (1990) Proc. Natl. Acad. Sci. (U.S.A.) 87:8923-8927). In this method, PCR is used to achieve the exponential amplification of target DNA, which is then detected using OLA.

In one aspect, the nucleic acid sequences of the gene of interest, or portions thereof, can be the basis for probes or primers, e.g., in methods for determining expression level of the gene of interest or the allelic variant of a polymorphic region of a gene of interest (KIR; HLA).

The methods of the disclosure can use nucleic acids isolated from vertebrates. In one aspect, the vertebrate nucleic acids are mammalian nucleic acids. In a further aspect, the nucleic acids used in the methods of the disclosure are human nucleic acids.

Primers for use in the methods of the disclosure are nucleic acids which hybridize to a nucleic acid sequence which is adjacent to the region of interest (KIR allele; HLA allele) or which covers the region of interest and is extended. A primer can be used alone in a detection method, or a primer can be used together with at least one other primer or probe in a detection method. Primers can also be used to amplify at least a portion of a nucleic acid. Probes for use in the methods of the disclosure are nucleic acids which hybridize to the gene of interest and which are not further extended. For example, a probe is a nucleic acid which hybridizes to the gene of interest, and which by hybridization or absence of hybridization to the DNA of a subject will be indicative of the identity of the allelic variant of the expression levels of the gene of interest. Primers and/or probes for use in the methods can be provided as isolated single stranded oligonucleotides or alternatively, as isolated double stranded oligonucleotides.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest (KIR; HLA).

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the disclosure will hybridize selectively to nucleotide sequences located about 100 to about 1000 nucleotides apart.

Yet other primers are nucleic acids which are capable of selectively hybridizing to the gene of interest. Thus, such primers can be specific for the gene of interest sequence, so long as they have a nucleotide sequence which is capable of hybridizing to the gene of interest.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids, or fragments thereof, to be used in the methods of the disclosure can be prepared according to methods known in the art. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

In some embodiments, determining the genotype of a KIR allele and/or determining the genotype of an HLA allele of an individual is performed at the request of a medical professional that performs the treatment, selection, or diagnosis described herein, Patient Selection Methods The present disclosure provides a method for selecting a multiple myeloma patient for a multiple myeloma therapy comprising an antibody specific to CD38, lenalidomide, and dexamethasone, comprising: (i) screening a biological sample (e.g., a tissue, cell or body fluid sample) isolated from the patient for the genotype of a killer Ig-like receptor (KIR) allele and a corresponding HLA class I ligand allele; and (ii) selecting the patient for the therapy if the genotype comprises the presence of the KIR allele with the absence of the corresponding HLA class I ligand allele. The presence of a 3DL1 KIR allele and/or an HLA-B Bw4-I80 allele indicates that the patient may be selected for treatment with an anti-CD38 antibody in combination with lenalidomide and dexamethasone.

The present disclosure provides a method for selecting a multiple myeloma patient for a therapy comprising an antibody specific to a tumor antigen, comprising: (i) screening a biological sample (e.g., a tissue, cell or body fluid sample) isolated from the patient for the genotype of a killer Ig-like receptor (KIR) allele and a corresponding HLA class I ligand allele; and (ii) selecting the patient for the therapy if the genotype comprises the presence of the KIR allele with the absence of the corresponding HLA class I ligand allele. The presence of a 3DL1 KIR allele and/or an HLA-B Bw4I-80 allele indicates that the patient may be selected for treatment with an anti-CD38 antibody.

The present disclosure provides a method of selecting an individual for a therapy comprising administering an anti-CD38 antibody, lenalidomide, and dexamethasone, wherein the individual has multiple myeloma, the method comprising: a) determining a genotype of a KIR allele in a biological sample obtained from the individual; b) determining a genotype of an HLA allele in a biological sample obtained from the individual; and c) selecting the individual for the therapy if determining of steps (a) and (b) indicates that the individual has a 3DL1 KR allele and an HLA-B Bw4I-80 allele.

In some cases, the multiple myeloma is relapsed multiple myeloma or refractory multiple myeloma Suitable biological samples include, e.g., a sample that comprises a nucleated blood cell or a peripheral blood lymphocyte.

Diagnostic Methods

The disclosure further provides diagnostic methods, which are based, at least in part, on determination of the identity of the allele types of the Killer Ig-like Receptors (KIR) genes and/or HLA genes.

For example, the present disclosure provides a method for identifying a multiple myeloma patient as likely to experience positive clinical outcome from a therapy comprising an anti-CD38 antibody, the method comprising: (i) screening a tissue, cell or body fluid sample isolated from the patient for the genotype of a killer Ig-like receptor (KIR) allele and a corresponding HLA class I ligand allele; and (ii) identifying the patient as likely to experience positive clinical outcome to the therapy if the genotype comprises the presence of the KIR allele with the absence of the corresponding HLA class I ligand allele. In some embodiments, the positive clinical outcome is selected from relatively high response or progression free survival as compared to patients not having the genotype.

The present disclosure provides a method of determining the likelihood that an individual having multiple myeloma will exhibit a beneficial clinical response to a treatment wherein the treatment comprises an anti-CD38 antibody, lenalidomide, and dexamethasone, the method comprising: a) determining a genotype of a killer Ig-like receptor (KIR) allele of the individual; b) determining a genotype of a human leukocyte antigen (HLA) allele of the individual, wherein the presence of a 3DL1 KIR allele, and the presence of an HLA Bw4I-80 allele, indicate that the individual has a greater likelihood of exhibiting a beneficial clinical response to the treatment, compared to an individual who does not have a KIR3DL1 allele and an HLA-B Bw4I-80 allele.

In some embodiments, the KIR allele encodes an inhibitory KIR gene. In some cases, the KIR allele is KIR3DL1. In some cases, the HLA allele is HLA-B Bw4I-80. In some cases, the HLA allele is HLA-B Bw4I-80; and is not HLA-B Bw4T80.

In some cases, the method further includes determining the level of beta-2 microglobulin (β2M) in the biological sample. A level of β2M at cycle 1, day 1 (baseline) that is less than 3.5 indicates increased likelihood of a beneficial clinical outcome.

Non-limiting samples to be screened include tissue or cells selected from non-metastatic tumor tissue, a non-metastatic tumor cell, metastatic tumor tissue, a metastatic tumor cell, blood or peripheral blood lymphocytes. In one aspect, patient sample comprises blood or a peripheral blood lymphocyte. For example, the patient sample can comprise nucleated cells. The patient sample includes sufficient patient DNA to allow for genotyping.

In these methods, responsiveness to therapy is measured by, e.g., a longer time of disease free survival, longer overall survival and/or lower risk of disease recurrence.

Information obtained using the diagnostic assays described herein is useful for determining if a subject will likely, more likely, or less likely to respond to cancer treatment of a given type. Based on the prognostic information, medical personnel can recommend a treatment regimen that will, or will not, include an anti-CD38 antibody, and may further include lenalidomide and/or dexamethasone.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: KIR and HLA Genotypes Influence Clinical Outcome in Multiple Myeloma Patients Treated with SAR650984 (Anti-CD38) in Combination with Lenalidomide and Dexamethasone Patients and Clinical Samples A Phase 1b study for evaluating the effects of a treatment with hu38SB19 combined with lenalidomide and low dose dexamethasone in patients with relapsed or refractory multiple myeloma was performed as described below.

The patients were treated with hu38Sb19 (also referred to as "SAR650984") combined with lenalidomide and dexamethasone, as described in WO 2014/089416. hu38SB19 was administered intravenously as a solution. Lenalidomide was administered orally as capsules. Dexamethasone was administered orally as tablets. The study duration for an individual patient included a screening period for inclusion of up to 21 days, and at least 4 weeks of treatment in the absence of severe adverse reaction, dose limiting toxicity or disease progression plus up to 60 days post-treatment follow up.

Whole blood samples (6 mL) were collected from patients enrolled in the phase 1b study prior to commencing treatment. The samples were collected into K2 EDTA VACUTAINER™ Plus tubes with HEMOGARD™ closure (Beckton Dickinson). The collected samples were kept on ice. Samples were stored at ⁻70° C. or colder, Samples were obtained from 31 patients, for which clinical response data was obtained for 28 patients. Patient consent to the correlative science portion of the protocols was obtained, allowing correlative studies on genomic DNA, hemoglobin, immunoglobulin (Ig) G/A/M, and free light chain.

Clinical Endpoints: Clinical data was analyzed by an intention-to-treat analysis (n=31). Time to progression (TTP) was determined from the start of treatment (cycle 1 day 1; C1D1) to disease progression, with deaths due to causes other than progression censored. Progression free survival (PFS) was determined from the start of treatment (C1D1) to disease progression or death (regardless of cause).

Objective response rate included complete response (CR), very good partial response (VGPR) and partial response (PR). Three patients were excluded for missing response data from early withdrawal (<6 weeks) due to adverse events. Z-test for proportions was used to analyze the data. Clinical benefit included CR, VGPR, PR, and minimal response (MR).

Response Criteria: Response criteria were based on the International Myeloma Working Group (IMWG) Uniform Response Criteria for Multiple Myeloma.

Sample Preparation: Peripheral blood was separated by Ficoll-Hypaque gradients and the peripheral blood mononuclear cells (PBMC) were isolated, counted, placed in designated aliquots, and frozen in liquid nitrogen for subsequent analysis.

Genotyping and Haplotyping: Genomic DNA was extracted from PBMCs using the QIAamp DNA minikit (Qiagen: Valencia, Calif.) according to the manufacturer's instructions. 100-200 nanograms of DNA/gene was obtained.

KIR gene loci were typed according to the standardized KIR typing method. Briefly, polymerase chain reaction (PCR)-sequence-specific primers (SSP) were designed to detect the genes encoding all known KIR alleles at a given locus, and to produce consistent results. PCR-SSP was used to determine the presence or absence of inhibitory KIR genes (KIR2DL1, 2DL2, 2DL3, 3DL1) and activating KIR genes (KIR2DS1, 2DS2, 2DS3, 2DS4, 2DS5, and 3DS1).

PCR primers were designed to capture all known alleles. 28 SSP for 13 KIR genes were used, with multiple primers for each individual KIR gene. For many KIR genes two different primer sets were used to establish presence or absence of the gene. Forward and reverse primers targeted sequences within exons 3 and 4, corresponding to Ig domains D0-2, with amplicon size in the range of 100-1000 base pairs. KIR2DL4, HLA-DR and DNA from KIR-genotyped reference cells were used as internal controls to confirm PCR amplifications.

KIR haplotypes were determined using previously published segregation patterns within families. Positive and negative linkage disequilibrium between KIR loci was used.

HLA alleles were identified by a combination of HLA serology, sequence-based amplification (PCR-SSP), and oligonucleotide probing of genomic DNA (PCR-sequence specific oligonucleotide probe [PCR-SSOP]).

Statistical Analysis: As a binary outcome, initial comparison of overall response for patients with the "missing ligand" KIR-HLA genotype and "ligand present" genotype were based on the chi-square test.

The Kaplan-Meier method was used to estimate progression-free survival and overall survival, and to compare the survival endpoints with the log-rank statistic. Because of the small sample size, no multiple testing adjustments were applied.

Results

NK cell subsets have different capacities for mediating antibody-dependent cell-mediated cytotoxicity (ADCC), depending on the strength of KIR/HLA interactions. To test whether KIR and HLA class I genotypes in multiple myeloma (MM) patients can predict responses to antibody treatment and serve as a prognostic tool, KIR and HLA class I genotypes were compared to clinical outcomes in MM patients treated with SAR650984, lenalidomide, and dexamethasone. The SAR650984, lenalidomide, and dexamethasone treatment may be referred to herein as "SAR/len/dex."

Figure 2:
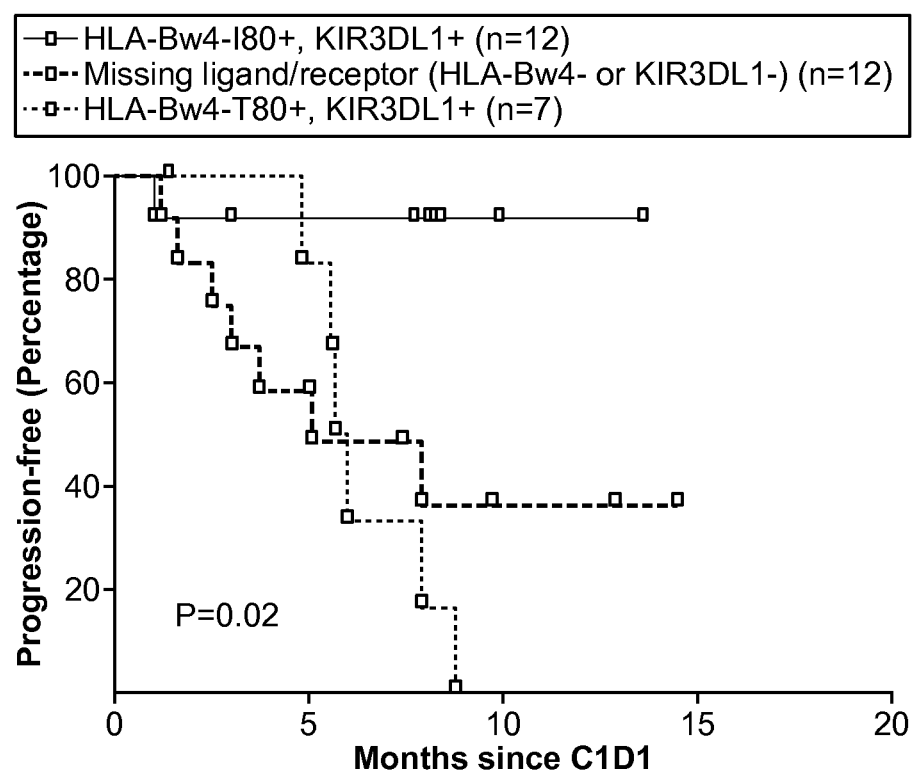
FIG. 2 shows the percentage of progression-free survival (PFS) of multiple myeloma (MM) patients treated with SAR650984 in combination with lenalidomide and dexamethasone (SAR/len/dex), classified according to HLA-Bw4 and KIR genotypes, as a function of months since cycle 1 day 1 (C1D1).
Figure 3:
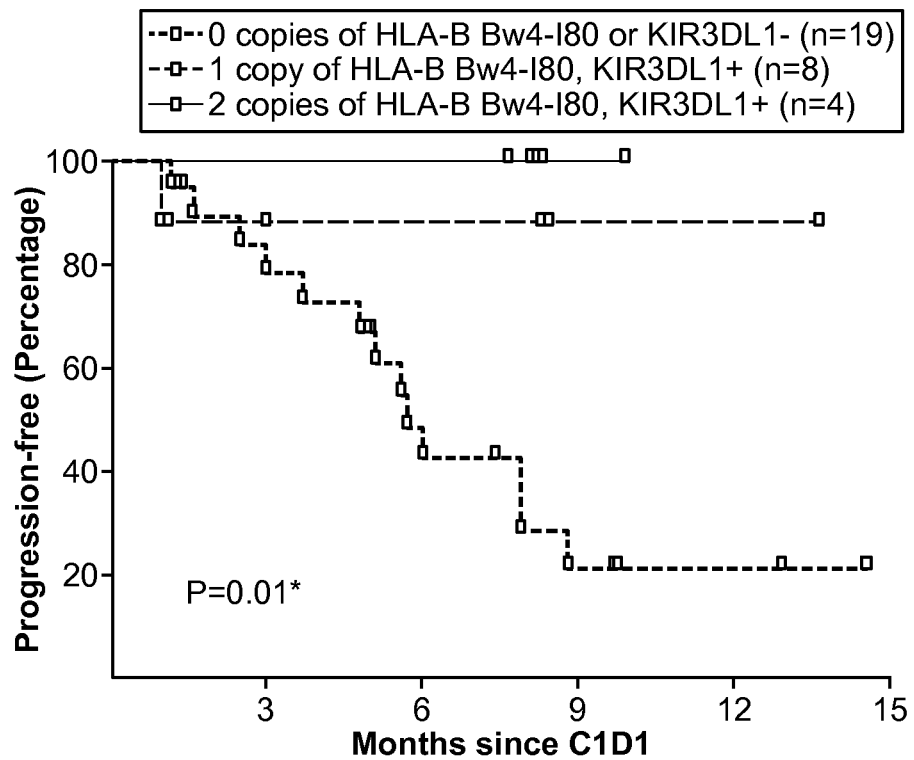
FIG. 3 shows the percentage of time to progression (TTP; top) and PFS (bottom) of MM patients treated with SAR/len/dex, classified according to the copy number of HLA-B Bw4-I80 and the KIR genotype, as a function of months since C1D1.
Figure 3:
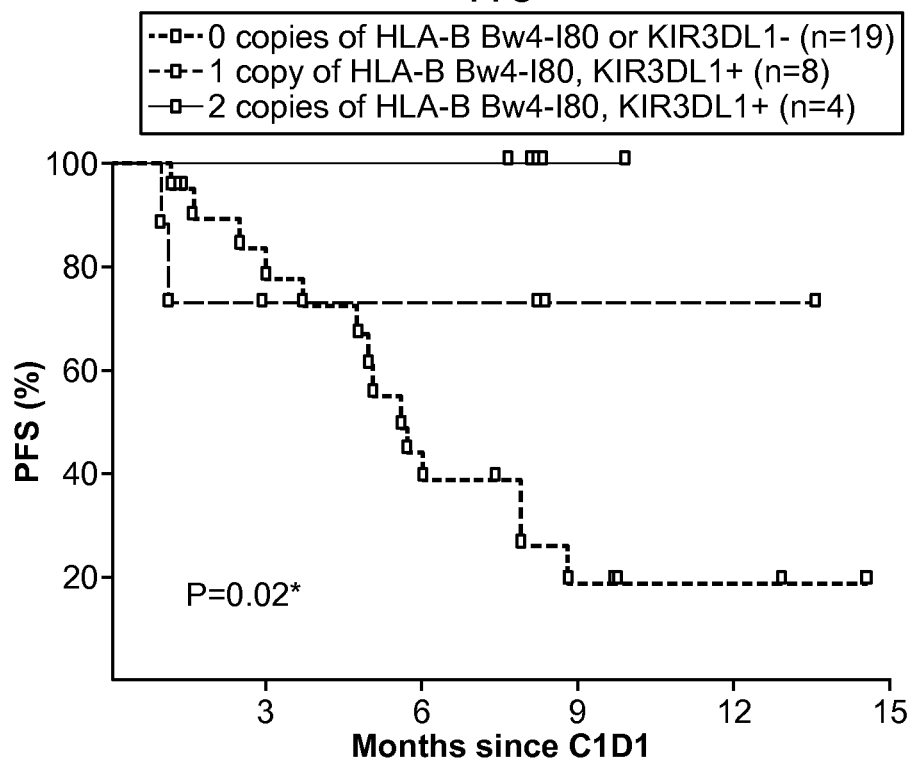

TTP and PFS (as shown in FIG. 2) were higher in SAR/len/dex-treated MM patients with high affinity KIR3DL1, HLA-Bw4-I80 ligand interactions compared to patients with low affinity KIR3DL1, HLA-Bw4-T80 ligand interactions. KIR3DL1, HLA-Bw4-I80 gene dose also correlated with prolonged TTP and PFS. As shown in FIG. 3, SAR/len/dex-treated MM patients with 2 copies of HLA-B Bw4-I80 had higher TTP and PFS compared to patients with 0 copies of HLA-B Bw4-I80 or no KIR3DL1 receptor.

Figure 4:
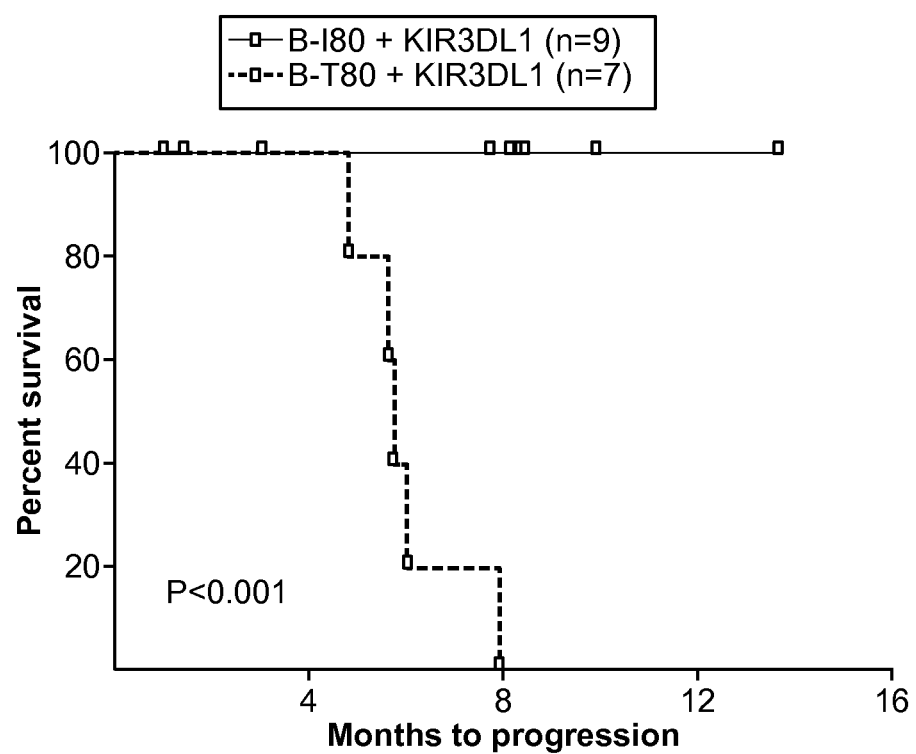
FIG. 4 shows the distinct outcomes among MM patients treated with SAR/len/dex, with HLA-Bw4-I80 and HLA-Bw4-T80 genotypes.

Distinct outcomes were observed among SAR/len/dex-treated MM patients with high affinity KIR3DL1, HLA-Bw4-I80 interactions and low affinity KIR3DL1, HLA-Bw4-T80 interactions (FIG. 4).

Figure 5:
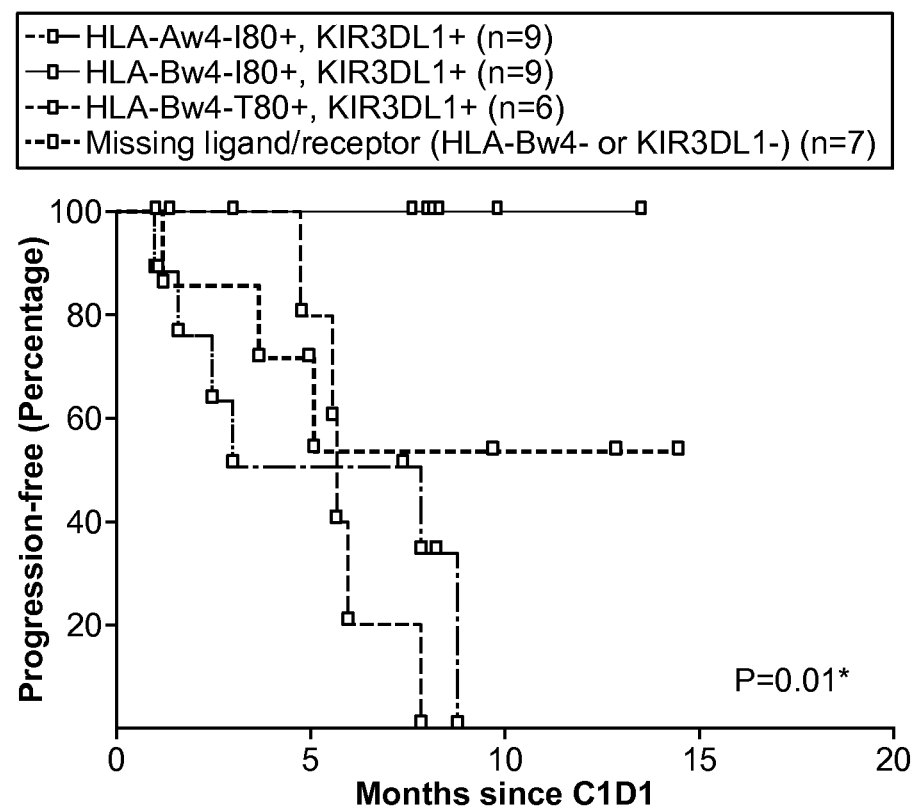
FIG. 5 shows the percentage of PFS of MM patients treated with SAR/len/dex, classified according to HLA and KIR genotypes, as a function of months since C1D1.

SAR/len/dex-treated MM patients with HLA-A ligands for KIR3DL1 showed rapid progression of disease, resembling the PFS rate of patients with low-affinity ligands (HLA-Bw4-T80) (FIG. 5).

Figure 6:
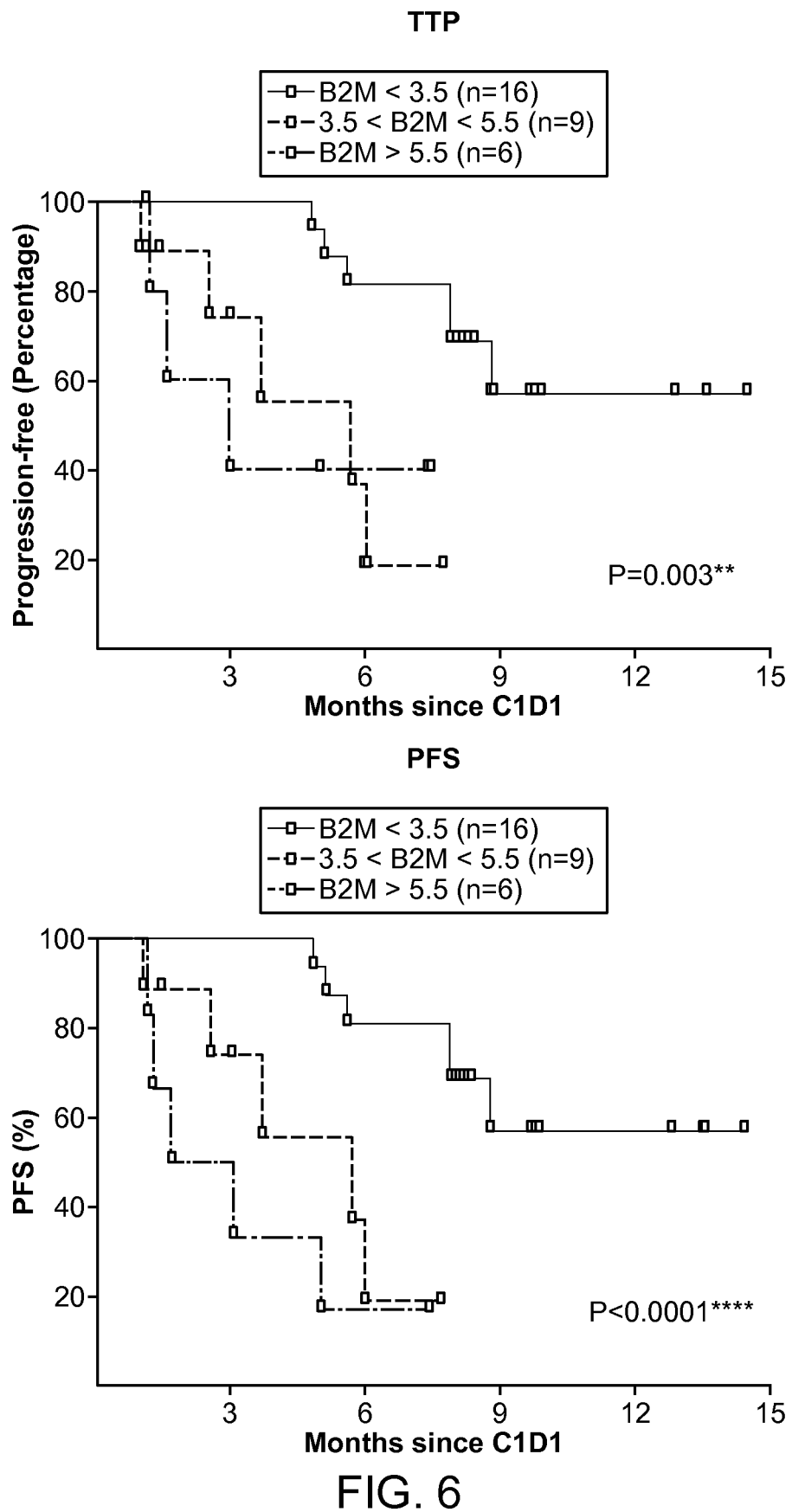
FIG. 6 shows the percentage of TTP (top) and PFS (bottom) of MM patients treated with SAR/len/dex, classified according to β2 microglobulin (B2M) levels at C1D1.
Figure 7:
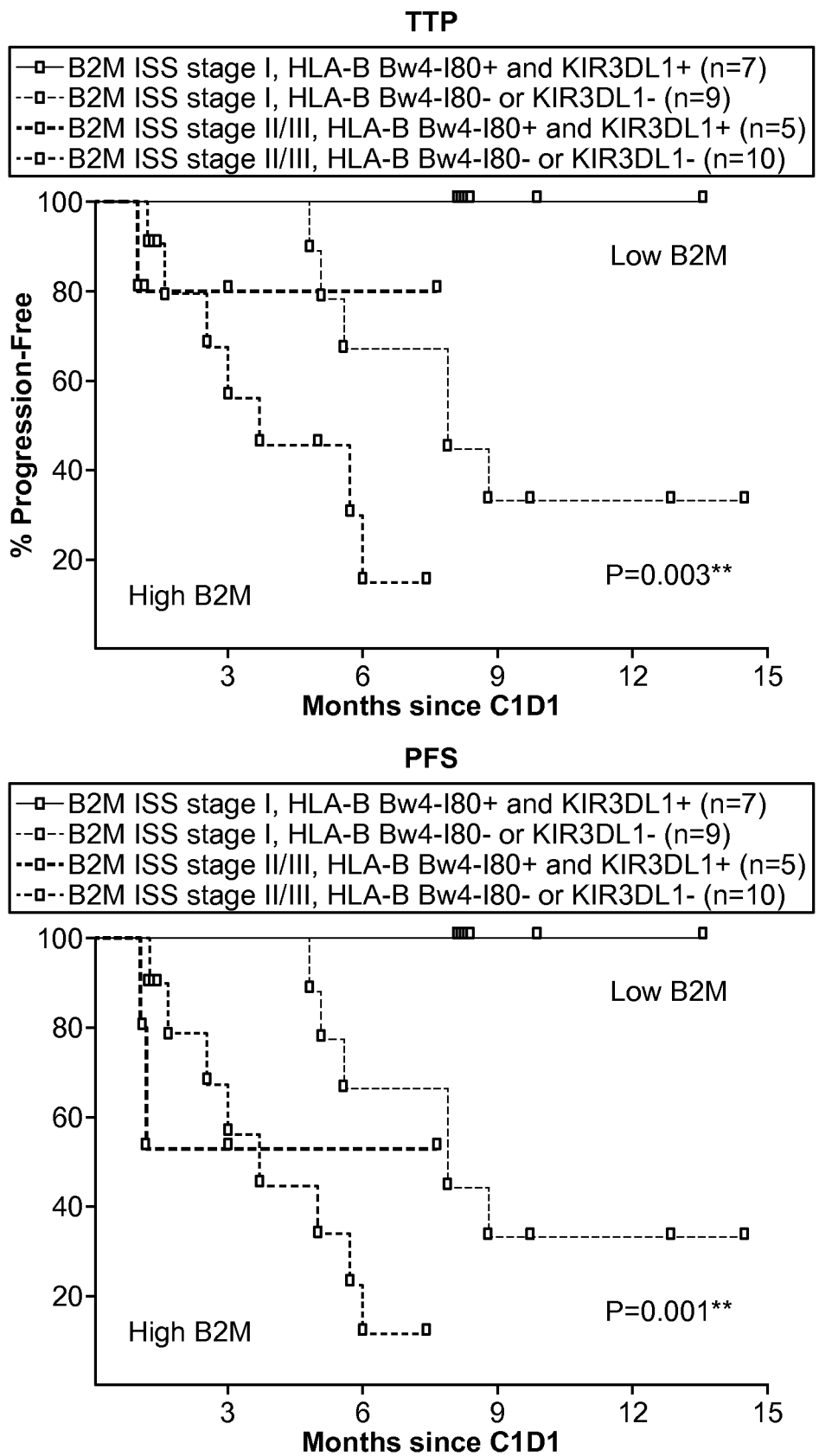
FIG. 7 shows the percentage of TTP (top) and PFS (bottom) of MM patients treated with SAR/len/dex, classified according to the B2M level, extent of the disease as defined by the International Staging System (ISS), and the HLA-Bw4 and KIR genotypes.

When SAR/len/dex-treated MM patients were classified according to β2M levels at C1D1, the β2M levels inversely correlated with prolonged TTP and PFS (FIG. 6). Thus β2M was prognostic for SAR/len/dex-treated MM patients. High affinity KIR3DL1, HLA-Bw4I80 interactions was also found to correlate with improved TTP and PFS among SAR/len/dex-treated MM patients with low β2M and high β2M (FIG. 7).

In summary, a KIR3DL1, HLA-B Bw4-80Ile genotype predictive of high-affinity NK cell receptor-ligand interactions and potent NK cell licensing correlated with increased ORR and PFS among patients treated with SAR/LEN/Dex.

Example 2: High Affinity Interactions Confer Potent NK Cell Licensing/Education and Antibody-dependent Cell-mediated Cytotoxicity (ADCC)

Figure 8:
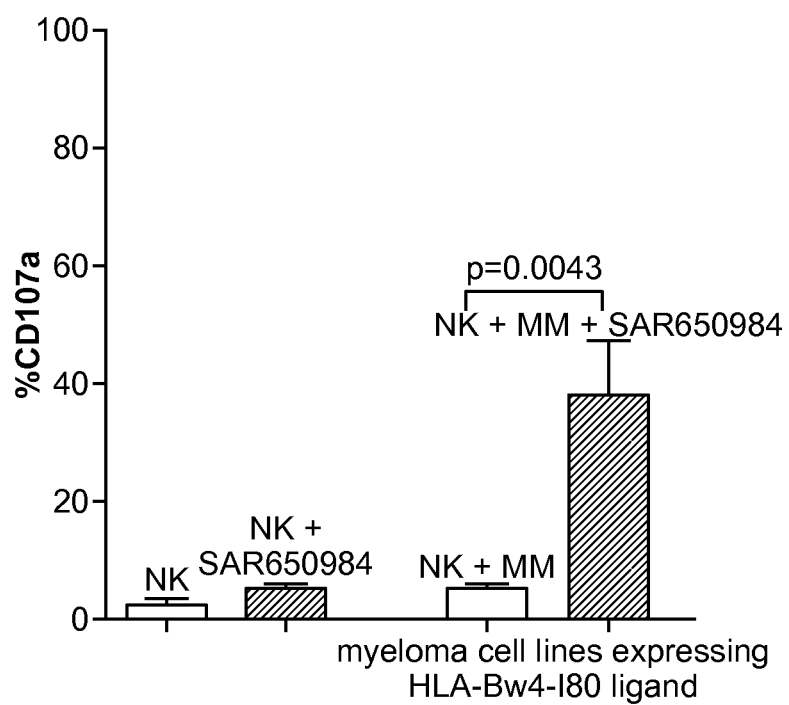
FIG. 8 shows percent degranulation (as measured by CD107α staining) induced by patient-derived myeloma target cells (MM) expressing the HLA-Bw4-I80 ligand in licensed KIR3DL1+ NK cells from MM patients, in the presence (filled bars) or absence (empty bars) of SAR650984.

The functional capacity of a patient's NK cells stimulated by pre-treatment patient-derived myeloma target cells was assessed in response to SAR650984, using flow cytometry (FIG. 8). In the presence of SAR650984, stimulation of licensed KIR3DL1+ NK cells by patient-derived myeloma target cell expressing HLA-Bw4-I80 ligand greatly enhanced degranulation, as measured by CD107α staining, which is a surrogate marker for cytotoxicity. This result suggests that SAR650984 can overcome HLA-Bw4 specific inhibition of licensed KIR3DL1+ NK cells in a genotype-specific manner, and that high affinity interactions between HLA ligand and KIR confer potent NK cell licensing/ education and ADCC.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an individual having multiple myeloma, the method comprising:
   a) determining a genotype of a KIR allele of the individual;
   b) determining a genotype of an HLA allele of the individual, and
   c) when said determining of steps (a) and (b) indicates that the individual has a 3DL1 KIR allele and an HLA-B Bw4-I80 allele, administering a treatment to the individual, wherein the treatment comprises an anti-CD38 antibody, lenalidomide, and dexamethasone, and wherein the anti-CD38 antibody comprises VHCDR1 of SEQ ID NO:1 (DYWMQ), VH CDR2 of SEQ ID NO:2 (TIYPGDGDTGYAQKFQG), VH CDR3 of SEQ ID NO:3 (GDYYGSNSLDY), VL CDR1 of SEQ ID NO:4 (KASQDVSTWA), VL CDR2 of SEQ ID NO:5 (SASYRYI), and VL CDR3 of SEQ ID NO:6 (QQHYSPPYT).

2. The method of claim 1, wherein the anti-CD38 antibody kills a CD38+ cell by apoptosis, by antibody-dependent cell-mediated cytotoxicity (ADCC), or by complement-dependent cytotoxicity (CDC).

3. The method of claim 1, wherein the anti-CD38 antibody binds CD38 with a kD of $3 \times 10^{-9}$ or greater.

4. The method of claim 1, wherein the anti-CD38 antibody comprises a humanized heavy chain framework region and/or a humanized light chain framework region.

5. The method of claim 1, wherein the anti-CD38 antibody comprises a VH region comprising the amino acid sequence set forth in SEQ ID NO:7, and comprises a VL region comprising the amino acid sequence set forth in SEQ ID NO:8.

6. The method of claim 1, wherein the anti-CD38 antibody comprises a heavy chain region of the isotype IgG1, IgG2, IgG3, or IgG4.

7. The method of claim 1, further comprising determining the copy number of the HLA-B Bw 4-I80 allele.

8. The method of claim 1, wherein said administering increases progression-free survival (PFS) and/or increases time to progression (TTP).

9. The method of claim 1, wherein the multiple myeloma is relapsed refractory multiple myeloma.

* * * * *

UNITED STATES PATENT AND TRADEMARK OFFICE
CERTIFICATE OF CORRECTION

PATENT NO. : 10,617,757 B2
APPLICATION NO. : 15/502182
DATED : April 14, 2020
INVENTOR(S) : Jeffrey M. Venstrom Page 1 of 1

It is certified that error appears in the above-identified patent and that said Letters Patent is hereby corrected as shown below:

In the Claims

In Claim 1, Line 61, "(KASQDVSTWA)," should read --(KASQDVSTVVA),--

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 15

<210> SEQ ID NO 1
<211> LENGTH: 5
<212> TYPE: PRT
<213> ORGANISM: Artificial sequence
<220> FEATURE:
<223> OTHER INFORMATION: Synthetic Peptide

<400> SEQUENCE: 1

Asp Tyr Trp Met Gln
1               5

<210> SEQ ID NO 2
<211> LENGTH: 17
<212> TYPE: PRT

```
<213> ORGANISM: Artificial sequence
<220> FEATURE:
<223> OTHER INFORMATION: Synthetic Peptide

<400> SEQUENCE: 2

Thr Ile Tyr Pro Gly Asp Gly Asp Thr Gly Tyr Ala Gln Lys Phe Gln
1               5                   10                  15

Gly

<210> SEQ ID NO 3
<211> LENGTH: 11
<212> TYPE: PRT
<213> ORGANISM: Artificial sequence
<220> FEATURE:
<223> OTHER INFORMATION: Synthetic Peptide

<400> SEQUENCE: 3

Gly Asp Tyr Tyr Gly Ser Asn Ser Leu Asp Tyr
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic Peptide

<400> SEQUENCE: 4

Lys Ala Ser Gln Asp Val Ser Thr Val Val Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic Peptide

<400> SEQUENCE: 5

Ser Ala Ser Tyr Arg Tyr Ile
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic Peptide

<400> SEQUENCE: 6

Gln Gln His Tyr Ser Pro Pro Tyr Thr
1               5

<210> SEQ ID NO 7
<211> LENGTH: 450
<212> TYPE: PRT
<213> ORGANISM: Artificial sequence
<220> FEATURE:
<223> OTHER INFORMATION: Synthetic Peptide

<400> SEQUENCE: 7

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30
```

```
Trp Met Gln Trp Val Lys Gln Arg Pro Gly Gln Gly Leu Glu Trp Ile
         35                  40                  45
Gly Thr Ile Tyr Pro Gly Asp Gly Asp Thr Gly Tyr Ala Gln Lys Phe
 50                  55                  60
Gln Gly Lys Ala Thr Leu Thr Ala Asp Lys Ser Ser Lys Thr Val Tyr
 65                  70                  75                  80
Met His Leu Ser Ser Leu Ala Ser Glu Asp Ser Ala Val Tyr Tyr Cys
                 85                  90                  95
Ala Arg Gly Asp Tyr Tyr Gly Ser Asn Ser Leu Asp Tyr Trp Gly Gln
                100                 105                 110
Gly Thr Ser Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
```

<210> SEQ ID NO 8
<211> LENGTH: 214
<212> TYPE: PRT
<213> ORGANISM: Artificial sequence
<220> FEATURE:
<223> OTHER INFORMATION: Synthetic Peptide

<400> SEQUENCE: 8

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 5
<212> TYPE: PRT
<213> ORGANISM: Artificial sequence
<220> FEATURE:
<223> OTHER INFORMATION: Synthetic Peptide

<400> SEQUENCE: 9

```
Ser Phe Ala Met Ser
1               5
```

<210> SEQ ID NO 10
<211> LENGTH: 16
<212> TYPE: PRT
<213> ORGANISM: Artificial sequence
<220> FEATURE:
<223> OTHER INFORMATION: Synthetic Peptide

<400> SEQUENCE: 10

```
Ala Ile Ser Gly Ser Gly Gly Gly Thr Tyr Tyr Ala Asp Ser Val Lys
1               5                   10                  15
```

<210> SEQ ID NO 11
<211> LENGTH: 13
<212> TYPE: PRT
<213> ORGANISM: Artificial sequence
<220> FEATURE:
<223> OTHER INFORMATION: Synthetic Peptide

<400> SEQUENCE: 11

Asp Lys Ile Leu Trp Phe Gly Glu Pro Val Phe Asp Tyr
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic Peptide

<400> SEQUENCE: 12

Arg Ala Ser Gln Ser Val Ser Ser Tyr Leu Ala
1               5                   10

<210> SEQ ID NO 13
<211> LENGTH: 7
<212> TYPE: PRT
<213> ORGANISM: Artificial sequence
<220> FEATURE:
<223> OTHER INFORMATION: Synthetic Peptide

<400> SEQUENCE: 13

Asp Ala Ser Asn Arg Ala Thr
1               5

<210> SEQ ID NO 14
<211> LENGTH: 10
<212> TYPE: PRT
<213> ORGANISM: Artificial sequence
<220> FEATURE:
<223> OTHER INFORMATION: Synthetic Peptide

<400> SEQUENCE: 14

Gln Gln Arg Ser Asn Trp Pro Pro Thr Phe
1               5                   10

<210> SEQ ID NO 15
<211> LENGTH: 362
<212> TYPE: PRT
<213> ORGANISM: Homo sapiens

<400> SEQUENCE: 15

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
                20                  25                  30

Tyr Thr Ser Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Cys Lys Thr Asn Thr Gln
                85                  90                  95

-continued

```
Thr Tyr Arg Glu Asn Leu Arg Ile Ala Leu Arg Tyr Tyr Asn Gln Ser
            100                 105                 110

Glu Ala Gly Ser His Thr Leu Gln Arg Met Tyr Gly Cys Asp Val Gly
            115                 120                 125

Pro Asp Gly Arg Leu Leu Arg Gly His Asn Gln Phe Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Thr Tyr Leu Glu Gly Thr Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Ser Ser Asp Ser
            340                 345                 350

Ala Gln Gly Ser Asp Val Ser Leu Thr Ala
            355                 360
```